United States Patent

Markowitz et al.

[11] Patent Number: 5,773,303
[45] Date of Patent: Jun. 30, 1998

[54] PROCESS AND KIT TO INITIATE A LUMINIFEROUS REACTION

[75] Inventors: Gerd Markowitz; Dierck Lentfer, both of Rodgau, Germany

[73] Assignee: BYK-Sangtec Diagnostica GmbH & Co. KG, Dietzenbach, Germany

[21] Appl. No.: 894,328

[22] PCT Filed: Feb. 14, 1996

[86] PCT No.: PCT/EP96/00628

§ 371 Date: Aug. 18, 1997

§ 102(e) Date: Aug. 18, 1997

[87] PCT Pub. No.: WO96/25516

PCT Pub. Date: Aug. 22, 1996

[30] Foreign Application Priority Data

Feb. 17, 1995 [DE] Germany ......................... 195 05 393.1

[51] Int. Cl.⁶ .................................................. G01N 21/76
[52] U.S. Cl. ............................ 436/172; 422/61; 435/810; 435/8
[58] Field of Search .................................. 422/61; 436/8, 436/172; 435/8, 4, 192, 810

[56] References Cited

U.S. PATENT DOCUMENTS

| | | | |
|---|---|---|---|
| 4,871,660 | 10/1989 | Gadow | 436/63 |
| 5,454,194 | 10/1995 | Otakiri et al. | 435/7.9 |
| 5,494,827 | 2/1996 | Oh et al. | 436/172 |
| 5,576,212 | 11/1996 | Honzawa et al. | 436/8 |
| 5,677,140 | 10/1997 | Denzler | 435/34 |

FOREIGN PATENT DOCUMENTS

| | | |
|---|---|---|
| 0186751 | 7/1986 | European Pat. Off. . |
| 3439742 | 4/1986 | Germany . |
| 58124935 | 7/1983 | Japan . |

OTHER PUBLICATIONS

Jones, P. et al "Kinetics and mechanism of catalysis by ferrihemes in the chemiluminogenic oxidation of luminol by hydrogen peroxide" Chemical Abstracts, vol. 107, No. 5 (1987) abstract No. 39496u.

Frew, J.E. et al "Assay of same clinically important reductants by a chemiluminescence delay technique" Chemical Abstracts, vol. 103, No. 25 (1985) abstract No. 210411f.

Schroeder et al., *Analytical Chemistry*, ,"Chemiluminescence Yields and Detection Limits of Some Isoluminol Derivatives in Various Oxidation Systems", vol. 50, No. 8, 1114–1120, Jul. 1978.

*Primary Examiner*—Jeffrey Snay
*Attorney, Agent, or Firm*—Jacobson, Price, Holman & Stern, PLLC

[57] ABSTRACT

A starter kit to initiate luminiferous reaction by oxidation of luminescent molecules in analytic tests comprises a neutral to slightly acidly reacting aqueous solution of hydrogen peroxide and an alkaline aqueous solution of deuteroferriheme. The components of the starter kit are characterized by great stability.

2 Claims, No Drawings

PROCESS AND KIT TO INITIATE A LUMINIFEROUS REACTION

TECHNICAL FIELD

The invention relates to a starter kit to initiate luminiferous reaction by oxidation of luminescent molecules in analytical tests.

PRIOR ART

Light-emitting chemical reactions have various uses in analytical tests. In clinical analysis, they have found wide use, in particular in immunoassays, in protein blotting and in DNA samples. The most successful tests include those in which the luminescent molecules employed are isoluminol derivatives and acridinium derivatives which give off energy in the form of light quanta in alkaline solution with consumption of peroxide. Particularly in the case of isoluminol derivatives, this reaction is subject to very slow kinetics. In order that a measurable amount of light is released in a reasonable time, catalysts are added. These catalysts mostly contain complexed iron. Beside potassium ferricyanide or ferrocyanide, compounds such as microperoxidase, hemin, hematin or enzymes such as catalase and horseradish peroxidase are described as suitable in the literature. In particular, catalase and microperoxidase have already been successfully used in commercial systems. In the case of isoluminol derivatives, ABEI (aminobutylethylisoluminol) or ABENH (aminobutylethylnaphthalenedicarboxylic hydrazide) have gained acceptance, since in contrast to luminol they can be coupled without problems to haptens or proteins without noticeable loss of quantum yield.

To measure the luminescence, suitable reagent solutions are pipetted into a solution containing the label in unknown amount in a measuring apparatus and the luminescence is immediately measured. The kinetics of the photoreactions of both classes of substance proceed in a few seconds under optimized conditions.

With luminescence becoming known in the literature, to initiate luminescence the procedure was originally used was to pipette three solutions: sodium hydroxide solution, catalyst and finally dilute hydrogen peroxide solution as oxidant [J. Clin. Chem. Clin. Biochem., 21, 789 (1983)]. With increasing commercialization of luminescence in immunoassays, a simplification of the light production was achieved by use of an alkaline peroxide solution (DE 3439742). The alkaline peroxide solution described is sufficiently stable for use in immunoassays within a given period of time after preparation, so that after addition of the catalyst the luminescence reaction is produced by injection of the alkaline peroxide solution into the measuring chamber. In an optimized variant which has been used commercially by the applicant for some years, the light yield can be increased in that first the alkaline peroxide solution is pipetted and then the catalyst starts the photo-reaction. The light yield is thereby again markedly increased. In both variants, the concentration of the sodium hydroxide solution used is very high (about 1M), as the light yield increases with increasing concentration. The combination of the two solutions of catalyst and peroxide is usually described as a starter kit.

A major problem of the starter kits used for light production is their restricted shelf-life. This has the consequence that in no case can they remain uncooled in an automatic measuring system for several days. For this reason, the solutions of a starter kit should if possible be completely used up on the same day or else stored in a refrigerator in the meantime at 2°–8° C. Stability investigations have shown that the usual liquid solutions can only be used for a maximum of 14 days even under optimum storage conditions. After this time, particularly due to the known light and temperature sensitivity of hydrogen peroxide in alkaline solution, on the one hand a marked decrease in the luminescence signal and on the other hand an increase in the nonspecific reagent blank value are to be observed. Thus the noise/signal ratio becomes markedly worse with increasing aging of the usual solutions, which markedly restricts their use in routine operation or in an automatic immunoassay analyzer.

Starter solutions are therefore also not offered for sale in ready-to-use form in commercial test systems, but must be brought into the ready-to-use form before the actual light measurement by the user. On the one hand, this means some unavoidable pipetting steps or the dissolution of a perhydride tablet (urea peroxide) in the appropriate solvent; on the other hand, it means a possible source of error in the manual preparation for a luminescence measurement by the operating personnel.

For the technical background, reference is made to EP-B 0186751.

DESCRIPTION OF THE INVENTION

The object of the present invention is to be seen as improving a starter kit to initiate luminiferous reaction by oxidation of luminescent molecules in the presence of catalysts in analytical tests such that the two components can be made available in ready-to-use solutions which remain stable for several months. A further aim of the invention is to be seen as designing the two components of a starter kit such that they can be employed directly in automatic luminescence analysis equipment for a relatively long time without additional preparation steps.

It has now surprisingly been found that these objects can be achieved by a starter kit comprising as oxidant a neutral-to weakly acidic-reacting aqueous solution with 0.01 to 0.1% by weight of hydrogen peroxide and as catalyst an alkaline aqueous solution of deuteroferriheme with a pH above 12.

The new starter kit can be employed directly in automatic luminescence analysis equipment. Owing to the accelerated kinetics which can be achieved using the new starter kit, the period of time for the photoreaction can be reduced, which makes possible increased sample throughput, in particular in completely automatic analyzer systems.

The advantageous properties of the new starter kit are surprising, as it was not expected that organic compounds would be stable for months in about 1M sodium hydroxide solution. In fact, the microperoxidase preferably used up to that point showed itself to be unsuitable according to the invention. With deuteroferriheme (DFH), however, a compound was found which completely fulfills the stability and light-measuring technical requirements. The synthesis of DFH is carried out by reaction of hemin with resorcinol according to the procedure of P. Jones et al. from J. of Chemical Education 64, 70 (1987). The product obtained after recrystallizing fulfills the requirements according to the invention.

The invention therefore relates to a starter kit to initiate luminiferous reaction by oxidation of luminescent molecules in analytical tests comprising oxidants and catalysts, wherein as oxidant hydrogen peroxide is present in a concentration of from 0.01 to 0.1% by weight in distilled water and as catalyst deuteroferriheme is present in an amount of from 200 to 3000 ng/ml in 0.1 to 2N aqueous sodium hydroxide solution.

Further subjects to which the invention relates follow from the patent claims.

The hydrogen peroxide used in combination with the new alkaline catalyst solution for light measurement can now be used in weakly acidic or neutral solution and can be kept therein in the usual form for over a year without loss of activity. As a secondary effect, the concentration can be kept lower, which additionally markedly positively affects the reagent blank value. In the first component of the starter kit according to the invention, hydrogen peroxide is now present in a concentration of from 0.01 to 0.1, preferably 0.03 to 0.04, % by weight in aqueous solution. The first component is preferably prepared by diluting an aqueous hydrogen peroxide solution with distilled water. In the second component of the starter kit according to the invention, deuteroferriheme is present in a concentration of from 200 to 3000, preferably 600 to 1000, ng/ml in 0.01 to 2N, preferably 0.5 to 1.5N, aqueous sodium hydroxide solution. The sequence of the injections of the two starter solutions has only a small effect on the result of measurements, but the addition of the oxidation solution before the catalyst solution is preferred because of the higher light yield and also the more rapid kinetics of the light reaction compared with the conventional variant. The measuring time can thereby be reduced and the throughput increased.

Over several months, both ready-to-use solutions showed neither a loss of the catalytic activity nor an increase in the nonspecific background, which in the use of these reagents in immunological test systems is essentially responsible for the sensitivity of the immunological test kits concerned. Owing to the preparation of solutions no longer being necessary, these reagents are not only more simple to handle but also no longer involve a possible danger of confusion during their preparation.

The stability of the two ready-to-use components of the starter kit according to the invention was investigated at room temperature and at 37° C. with the example of an immunoluminometric assay for PSA (prostate specific antigen) on the fully automatic luminescence analyzer LIAmat S 300 (Byk-Sangtec Diagnostica). Even after 6 months, neither a loss of assay sensitivity nor a reduction in the maximum luminescence signal resulted.

We claim:

1. A starter kit to initiate luminiferous reaction by oxidation of luminescent molecules in analytical tests comprising oxidants and catalysts, wherein as oxidant hydrogen peroxide is present in a concentration of from 0.01 to 0.1% by weight in distilled water and as catalyst deuteroferriheme is present in an amount of from 200 to 3000 ng/ml in 0.1 to 2N aqueous sodium hydroxide solution.

2. A procedure to initiate the luminiferous reaction by oxidation of luminescent molecules in analytical tests, which comprises first adding a neutral- to weakly acidic-reacting aqueous solution of hydrogen peroxide and then an alkaline aqueous solution of deuteroferriheme having a pH of at least 12.

* * * * *